United States Patent [19]

Goodwin-Johansson

[11] Patent Number: 5,740,258
[45] Date of Patent: Apr. 14, 1998

[54] ACTIVE NOISE SUPRESSORS AND METHODS FOR USE IN THE EAR CANAL

[75] Inventor: Scott H. Goodwin-Johansson, Pittsboro, N.C.

[73] Assignee: MCNC, Research Triangle Park, N.C.

[21] Appl. No.: 461,001

[22] Filed: Jun. 5, 1995

[51] Int. Cl.$^6$ .......................... H03B 29/00; A61F 11/06; H04R 25/00
[52] U.S. Cl. .................. 381/72; 381/71; 381/94; 381/68.6
[58] Field of Search .................. 381/72, 94, 71, 381/73.1, 68, 68.6, 68.2, 68.4, 191

[56] References Cited

U.S. PATENT DOCUMENTS

| | | | |
|---|---|---|---|
| 2,972,018 | 12/1961 | Hawley et al. | 179/1 |
| 3,890,474 | 6/1975 | Glicksberg | 179/107 |
| 4,061,875 | 12/1977 | Freifeld et al. | 179/1 |
| 4,455,675 | 6/1984 | Bose et al. | 381/74 |
| 4,833,719 | 5/1989 | Carme et al. | 381/72 |
| 4,947,434 | 8/1990 | Ito | 381/71 |
| 4,953,217 | 8/1990 | Twiney et al. | 381/71 |
| 4,985,925 | 1/1991 | Langberg et al. | 381/72 |
| 5,091,954 | 2/1992 | Sasaki et al. | 381/72 |
| 5,134,659 | 7/1992 | Moseley | 381/71 |
| 5,138,663 | 8/1992 | Moseley | 381/71 |
| 5,138,664 | 8/1992 | Kimura et al. | 381/71 |
| 5,267,321 | 11/1993 | Langberg | 381/72 |
| 5,276,740 | 1/1994 | Inanaga et al. | 381/187 |
| 5,305,387 | 4/1994 | Sapiejewski | 381/71 |
| 5,327,506 | 7/1994 | Stites III | 381/169 |
| 5,355,418 | 10/1994 | Kelsey et al. | 381/72 |
| 5,572,594 | 11/1996 | Devoe et al. | 381/68.6 |

FOREIGN PATENT DOCUMENTS

| | | |
|---|---|---|
| 2 172 769 | 3/1985 | United Kingdom . |
| 9430030 | 12/1994 | WIPO ........................... 381/68 |

OTHER PUBLICATIONS

Technology News, "Micromachined Mike Has Many Applications", *Solid State Technology,* p. 26, Mar. 1995.

Advertisement, "Now You Hear It . . . Now You Don't: Noisebuster", Noise Cancellation Technologies, Inc., USAir Magazine, p. 76 (Aug. 1994).

Daniel Sweeney, Sound Conditioning Through DSP, *Audio,* pp. 26–32, Mar. 1994.

Leo O'Oconnor, Generating the sounds of silence, *Mechanical Engineering,* p. 54, Apr. 1994.

Primary Examiner—Curtis Kuntz
Assistant Examiner—Xu Mei
Attorney, Agent, or Firm—Bell, Seltzer, Park & Gibson

[57] ABSTRACT

A noise suppressor includes an input transducer and an output transducer adapted to be located in an ear canal. A housing is provided to support the transducers in the ear canal, and the housing provides an acoustically unobstructed passage from the entrance of the ear canal to the ear drum. The input transducer generates electrical signals in response to sound pressure waves entering the ear canal, and a portion of the electrical signal is processed to generate an inverse noise signal which is applied to the output transducer. Accordingly, the output transducer produces inverse noise pressure waves in order to reduce an undesired noise portion of the sound pressure waves reaching the ear drum. The sound pressure waves also reach the ear drum without significant alteration.

31 Claims, 1 Drawing Sheet

U.S. Patent   Apr. 14, 1998   5,740,258
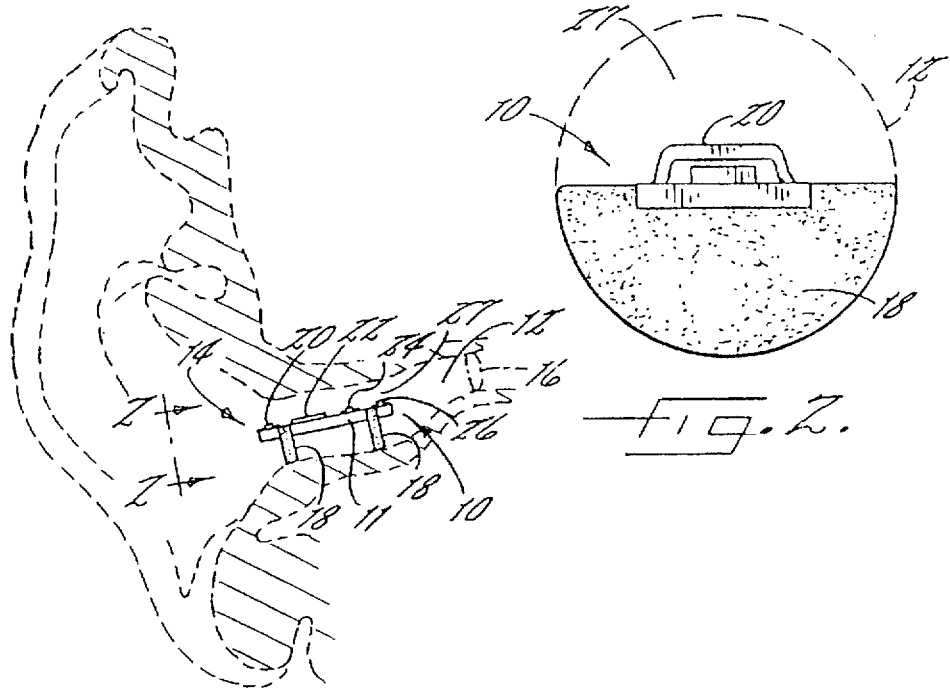
Fig. 1.
Fig. 2.
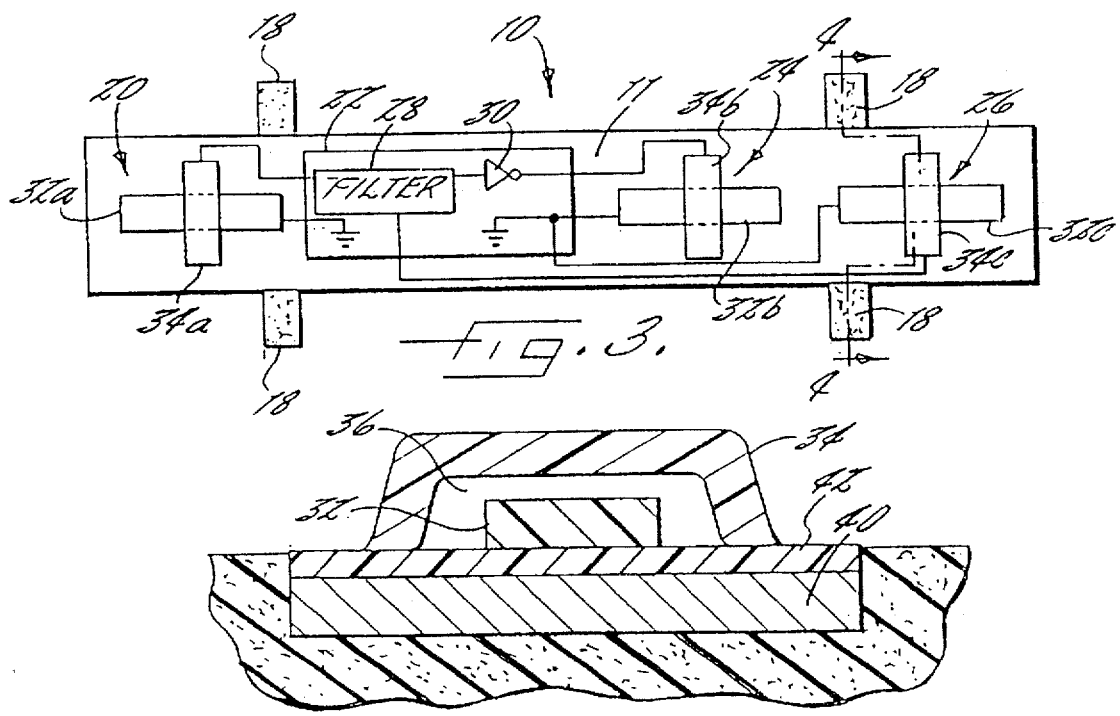
Fig. 3.
Fig. 4.

1

ACTIVE NOISE SUPRESSORS AND METHODS FOR USE IN THE EAR CANAL

FIELD OF THE INVENTION

This invention relates to the field of noise suppressors and more particularly to active noise suppressors.

BACKGROUND OF THE INVENTION

Ear plugs are commonly used to reduce the level of sounds entering the ear canal of a user thereby reducing the volume of sounds heard. Conventional ear plugs typically block the ear canal with a sound absorbing material. Accordingly, all sounds, including undesired noise as well as desired sounds such as speech, may be attenuated. In addition, conventional ear plugs may not effectively block low frequency noises.

Active noise cancellation has been another approach to noise reduction. In principle, active noise reduction cancels unwanted sounds by generating anti-noise signals through an amplifier and speaker. A microphone picks up the sound to be canceled, a processor generates an inverse replica of the noise, and an amplifier and loudspeaker generate anti-noise at the same acoustical power as the processed anti-noise itself. When the original and inverted noises meet, they cancel. In practice, however, the processing required is usually quite sophisticated. This technique may also be difficult to implement in a large area such as a room.

For example, U.K. Patent Application No. 2,172,769 A entitled "Ear Defender" discloses a device comprising a microphone located upstream of a loudspeaker relative to the direction of approach of unwanted intrusive noise, in an assembly adapted to be mounted at a site of entry of the noise into the ear chamber. The output of the microphone is amplified and fed to the downstream loudspeaker to produce noise which tends to cancel the unwanted intrusive noise. The device is attached by means of a headband.

U.S. Pat. No. 4,985,925 to Langberg et al. entitled "Active Noise Reduction System" discloses an electronic ear plug seated in the concha fossa combining active and passive noise reduction in the quiet zone at the ear. In this patent, the electronic earplug maintains an acoustical seal with a concha fossa (the hollow which is external to the opening of the ear canal) and/or the external auditory meatus (ear canal). Noise which penetrates this passive barrier and reaches the quiet zone formed around the occluded ear canal volume adjacent the ear drum, is further reduced by active means.

U.S. Pat. No. 3,890,474 to Glicksberg entitled "Sound Amplitude Limiters" discusses the incorporation of sound amplitude limiting into a device which is self-contained in the ear canal of the user. In this patent, the sound amplitude limiter is designed so that most un-transduced sound is blocked out from reaching the middle ear by a highly effective sound absorbing material which is located within the ear piece which is situated in the ear canal.

U.S. Pat. No. 5,355,418 to Kelsey et al. entitled "Frequency Selective Sound Blocking System for Hearing Protection" discusses a frequency selective hearing protection device. When worn in the manner shown, this device performs a natural sound blocking function. It utilizes adaptive filtering to hinder the transmission of frequency components in ambient sound above a predetermined threshold.

U.S. Pat. No. 5,305,387 to Sapiejewski entitled "Earponing" discusses an earphone for use in an active noise reduction system. This earphone includes a shell accommodating a microphone closely adjacent to a driver shaped and sized to fit in the concha of an ear. A cushion is made of silicon gel covered by polyurethane film and is shaped to provide comfort and seal to different ears without moving the microphone away from the ear canal.

In addition, the article entitled "Micromachined Mike has Many Applications" in *Solid State Technology*, p. 26, March 1995, discusses a micromachined silicon microphone. The device is formed on a 3 mm$^2$ chip in a 4 pin surface mount package. About 20 percent of the die area is taken up by the microphone diaphragm, which moves in an etched cavity, and a JFET amplifier is also incorporated on the device.

Notwithstanding the above mentioned references, there continues to exist a need in the art for a noise suppressor which reduces the level of undesired noise heard by the user without obstructing the passage of desired sounds.

SUMMARY OF THE INVENTION

It is therefore an object of the present invention to provide an improved noise suppressor.

It is another object of the present invention to provide an active noise suppressor which fits in an ear canal.

These and other objects are provided, according to the present invention, by a noise suppressor, including input and output transducers, which fits in the ear canal while maintaining an acoustically unobstructed path from the entrance of the ear canal to the ear drum. The input transducer generates an electrical signal responsive to sound pressure waves entering the ear canal, and the output transducer generates inverse noise pressure waves to thereby reduce an undesired noise portion of the sound pressure waves reaching the ear drum. The desired portions of the sound pressure waves reach the ear drum through the acoustically unobstructed path thereby allowing the reduction of undesired noise portions without degrading the quality of the desired portions. In addition, the use of microelectromechanical transducers allows the input and output transducers to be fabricated on a common substrate which can fit in an ear canal. By locating the transducers in the ear canal, inverse noise pressure waves can be more accurately produced in close proximity to the ear drum.

Accordingly, in one embodiment of the present invention a noise suppressor selectively reduces an undesired noise portion of sound pressure waves in an ear canal having an entrance and an ear drum. This noise suppressor includes an input transducer which generates an electrical signal in response to the sound pressure waves in the ear canal, and an output transducer which produces inverse noise pressure waves in the ear canal. The inverse noise pressure waves are approximately out of phase with respect to the undesired noise portion of the sound pressure waves, thereby reducing the undesired noise portion of the sound pressure waves reaching the ear drum. The input and output transducers are supported in a housing which defines an acoustically unobstructed passage for the sound pressure waves from the entrance of the ear canal to the ear drum. As discussed above, the acoustically unobstructed passage allows the active reduction of the undesired noise portions without degrading the desired portions of the sound pressure waves reaching the ear drum. Stated in other words, desired portions of the sound pressure waves reach the ear drum without being reproduced by the output transducer.

The noise suppressor may also include a feedback transducer which generates an error signal in response to a combination of the sound pressure waves and the inverse noise pressure waves. This feedback transducer is preferably adapted to be positioned in the ear canal between the output transducer and the ear drum. Accordingly, the operation of the noise suppressor can be modified to further reduce the undesired noise portion of the sound pressure waves.

In addition, the input transducer is preferably adapted to be positioned in the ear canal adjacent the entrance and the output transducer is preferably adapted to be positioned in the ear canal between the input transducer and the ear drum. Accordingly, the sound pressure wave can be sampled as it enters the ear canal and the electrical signal processed as the sound pressure wave travels down the ear canal. The processed signal can then be applied to the output transducer which produces the inverse noise pressure signals as the sound pressure waves pass. This location of the output transducer also allows the inverse noise pressure waves to be produced adjacent the ear drum thereby reducing the power required to be produced by the output transducer.

Each of the input and output transducers preferably includes a conductive layer defining a first capacitor electrode, and a diaphragm adjacent and spaced apart from the conductive layer defining a second capacitor electrode. In the case of the input transducer, the second capacitor electrode moves relative to the first capacitor electrode in response to the sound pressure waves, thereby generating the electrical signal. In the case of the output electrode, the second electrode moves relative to the first electrode in response to an output electrical signal applied therebetween, thereby producing the inverse noise pressure waves. Accordingly, these microelectromechanical transducers can be produced on a common substrate using standard microelectronic fabrication techniques.

Furthermore, each of the input and output transducers may comprise an array of microelectromechanical transducers, thereby allowing the noise suppressor to preserve a directional component of the noise portion of the sound pressure wave entering the ear canal. The noise suppressor may also include a processor which processes the electrical signal in order to generate an inverse noise signal which is applied to the output transducer. This processor preferably includes a filter for selectively passing a noise portion of the electrical signal, and this noise signal is representative of the undesirable noise portion of the sound pressure waves. The processor also preferably includes an invertor which inverts the noise signal to generate the inverse noise signal. Accordingly, only the undesirable portion of the sound pressure wave is canceled by the inverse noise signal.

BRIEF DESCRIPTION OF THE DRAWINGS

FIG. 1 is a side view of a noise suppressor according to the present invention positioned in an ear canal.

FIG. 2 is an end view of the noise suppressor of FIG. 1 taken along section line 2.

FIG. 3 is an enlarged top view of the noise suppressor substrate and electronic devices of FIG. 1.

FIG. 4 is a greatly enlarged cross-sectional side view of a microelectromechanical transducer according to the present invention.

DETAILED DESCRIPTION OF A PREFERRED EMBODIMENT

The present invention will now be described more fully hereinafter with reference to the accompanying drawings, in which a preferred embodiment of the invention is shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thickness of layers and regions are exaggerated for clarity. Like numbers refer to like elements throughout.

One embodiment of a noise suppressor 10 according to the present invention, is illustrated in FIG. 1. As shown, the noise suppressor 10 is adapted to be located in an ear canal 12 between the entrance 14 to the ear canal 12 and the ear drum 16. Accordingly, the noise suppressor is not visible when placed in the ear canal, and it is also located relatively close to the ear drum.

The noise suppressor 10 includes an input transducer 20, such as a microphone, adapted to be located near the entrance 14 of the ear canal 12 and which generates an electrical signal in response to sound pressure waves entering the ear canal 12. The noise suppressor also includes a processor 22 which generates an inverse noise signal in response to the electrical signal generated by the input transducer 20. The inverse noise signal is applied to the output transducer 24, such as a speaker, which produces an inverse noise pressure wave. This inverse noise pressure wave is approximately out of phase with respect to an undesired noise portion of the sound pressure wave so that the undesired noise portion of the sound pressure wave traveling down the ear canal is reduced at the ear drum. Accordingly, the user of the noise suppressor hears desired portions of the sound pressure waves at approximately full intensity while undesired noise portions of the sound pressure waves are heard at a reduced intensity.

By sampling the sound pressure waves and producing inverse noise pressure waves in the ear canal, the undesired noise portion of the sound pressure waves can be more accurately reduced than in more conventional active noise cancellation systems which operate in larger acoustical environments such as a room or even earphones. This is because the ear canal acts as a small duct where sound pressure waves approximate planar waves. These planar sound pressure waves can be sampled and the corresponding inverse noise pressure waves produced with more accuracy at the ear drum than is possible in larger systems.

The noise suppressor can also be used to selectively amplify desired portions of the sound pressure waves entering the ear canal. For example, the noise suppressor can be used as a hearing aid wherein undesired noise portions of the sound pressure waves are reduced at the ear drum as discussed above. In addition, the hearing aid can selectively amplify desired portions of the noise pressure waves such as speech. Alternately, the noise suppressor can be integrated with a communications system such as a radio. In this application, the output transducer can be used to produce signals generated by the radio in addition to inverse noise pressure waves which reduce undesired noise at the ear drum. Accordingly, the user can hear the sounds generated by the radio while reducing some or all of the sound pressure waves entering the ear canal.

The noise suppressor 10 is preferably implemented on a single substrate 11 on which the input transducer 20, the processor 22, and the output transducer 24 can be formed. The noise suppressor 10 also includes a mounting or housing to support the substrate 11 including the input transducer, the output transducer, and the processor. This housing may include elastic portions 18 attached to the substrate which lodge the substrate in the ear canal with the input transducer located near the entrance and the output transducer located between the input transducer and the ear drum. These elastic portions are preferably formed so that an acoustically unobstructed (or clear) passage is maintained through the ear canal.

Accordingly, the desired portions of the sound pressure waves pass through the acoustically unobstructed passage to the ear drum without being subject to significant passive attenuation. Because the desired portions are not passively blocked, and preferably are not reproduced by the output transducer, these desired portions of the sound pressure wave reach the ear drum with natural fidelity. Stated in other words, sound attenuation occurs as a result of the inverse noise pressure waves which do not significantly affect the desired portions of the sound pressure waves. The acoustically unobstructed passage 27 is shown in FIG. 2 where space exists between the noise suppressor and the sides of the ear canal.

The noise suppressor 10 may also include a feedback transducer 26, such as a microphone, located between the output transducer 24 and the ear drum 16. The feedback transducer 26 generates an error signal in response to the sound pressure waves and the inverse noise pressure waves, and this error signal is representative of an uncanceled portion of the noise portion of the sound pressure waves. This error signal can be applied to the processor 22 using feedback techniques well known to those having skill in the art, in order to adapt the operation of the noise suppressor so that the noise portion of the sound pressure waves can be further reduced.

Alternately, some or all of the processor 22 can be implemented in a separate unit. For example, the processor 22 can be implemented as a separate unit which is electrically connected to the unit in the ear canal. In addition, a power supply can be provided external to the ear canal and electrically connected thereto.

A greatly enlarged view of the noise suppressor 10 is illustrated in FIG. 3. As shown, each of the transducers 20, 24, and 26 can be implemented as a pair of capacitor electrodes 32a–c and 34a–c on a common substrate. The first electrode 32a–c is preferably a conductive layer such as a doped polysilicon layer on the substrate. The second electrode is preferably implemented as a flexible diaphragm spaced apart from the first electrode such that the second electrode is movable relative to the first electrode.

In the case of the input transducer 20 and the feedback transducer 26, the second electrodes 34a and 34c move relative to the first electrodes 32a and 32c in response to pressure waves acting on the respective second electrodes. By applying an electrical charge to one of the electrodes in a transducer, the voltage between the two electrodes of the transducer will change as the distance between the two electrodes changes. Accordingly, this voltage between the electrodes of the transducer can be used to determine the spacing of the electrodes at a specific time, and changes in the voltage can be used to generate an electrical signal representative of the pressure waves acting on the transducer.

In the case of the output transducer 24, the second electrode 34b moves relative to the first electrode 32b in response to an inverse noise signal applied between the two electrodes. The inverse noise signal applied to the electrodes is preferably generated by the processor 22, and this signal is preferably representative of an inverse of the undesired noise portion of the sound pressure wave entering the ear canal. Accordingly, the inverse noise pressure waves generated by the output transducer are approximately out of phase with respect to the undesired noise portion of the sound pressure waves entering the ear canal. The inverse noise pressure waves are preferably approximately 180° out of phase and approximately equal in amplitude with respect to the undesired noise portion of the sound pressure waves reaching the ear drum so that the undesired noise portion is significantly reduced at the ear drum.

As shown in FIG. 3, the processor 22 preferably includes a filter 28 and an invertor 30. The filter 28 receives electrical signals generated by the input transducer 20 which are representative of sound pressure waves entering the ear canal. These electrical signals are preferably filtered by filter 28 so that the filter output signal is representative of the undesired noise portion of the sound pressure waves entering the ear canal. The filter 28 can determine the undesired noise portion of the signal based on frequency, volume, repetitive sounds, etc. Accordingly, the portions of the signal generated by the input transducer which represent the desired portion of the sound pressure wave entering the ear canal are blocked by the filter.

The processor may also include an invertor 30 which inverts the filter output signal before applying it to the output transducer 24. The invertor insures that the inverse noise pressure waves produced by the output transducer are approximately out of phase with respect to the noise portion of the sound pressure waves. Accordingly, the invertor may reverse the polarity of the signal. The invertor can also include means for delaying the signal to take into account the time required for the sound pressure wave to travel from the input transducer to the output transducer. As discussed above, the processor 22 including filter 28 and invertor 30 can be implemented together with the transducers on a common substrate adapted to be positioned in the ear canal. Alternately, a portion or all of the processor can be implemented as a separate unit which is electrically connected to the transducers.

In addition, the processor can compensate for portions of the inverse noise pressure waves which are generated by the output transducer and received by the input transducer. This feature is useful because the inverse noise pressure waves are produced in close proximity to the input transducer, and the resulting ring-around could lead to an increase in noise. Accordingly, the filter can determine the ring-around portions of the signal generated by the input transducer which correspond to the inverse noise pressure waves produced by the output transducer. The filter can then block these portions of the signal to reduce ring-around.

A greatly enlarged cross sectional side view of a microelectromechanical transducer is illustrated in FIG. 4. As shown, the first electrode 32 and the second electrode 34 can be provided on a substrate which may include semiconductor layer 40 and passivation layer 42. The semiconductor layer may be a silicon layer, a gallium arsenide layer, a diamond layer, a silicon carbide layer, or other layers known to those having skill in the art. The passivation layer may be a silicon dioxide layer, a silicon nitride layer, a polyimide layer, or other layers known to those having skill in the art. If the transducers and processor are implemented on a common substrate, as discussed above, the semiconductor layer allows microelectronic devices such as transistors, resistors, and capacitors to be fabricated thereon. Alternately, the first and second electrodes of each transducer can be fabricated on a printed circuit board, a multi-level substrate, or other substrate known to those having skill in the art.

The second electrode 34 is shown implemented as a diaphragm separated from the first electrode 32 by an air gap 36. Accordingly, in an input or feedback transducer, the second electrode moves relative to the first electrode in response to sound pressure waves acting on the second electrode. Alternately, in an output transducer, the second electrode moves relative to the first electrode in response to an electrical signal applied between the two electrodes. These transducers can be fabricated as described below.

The passivation layer 42 is formed on the semiconductor layer 40 to protect the semiconductor layer. The first electrode 32 is preferably formed from a conductive material such as doped polysilicon. This first electrode is then covered with a sacrificial layer such as silicon dioxide, and this sacrificial layer is patterned to define a desired spacing between the first and second electrodes. The second electrode 34 is then formed on the passivation layer 42 and sacrificial layer. The sacrificial layer is then selectively removed to define the air gap 36. Accordingly, the processor can be formed on a semiconductor substrate and then the transducers can be fabricated on the same substrate to produce an integrated noise suppressor on a common substrate which can be adapted to fit in an ear canal.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A noise suppressor for selectively reducing an undesired noise portion of sound pressure waves in an ear canal having an entrance and an ear drum, said noise suppressor comprising:

an input transducer which generates an electrical signal in response to said sound pressure waves in said ear canal;

an output transducer which produces inverse noise pressure waves in said ear canal, said inverse noise pressure waves being approximately out of phase with respect to said undesired noise portion of said sound pressure waves, thereby reducing said undesired noise portion; and an acoustically unobstructing housing which supports said input transducer and said output transducer in said ear canal, said acoustically unobstructing housing defining a clear passage for said sound pressure waves from said entrance of said ear canal to said ear drum, thereby allowing said sound pressure waves to pass to said ear drum.

2. A noise suppressor according to claim 1 further comprising a feedback transducer which generates an error signal in response to a combination of said sound pressure waves and said inverse noise pressure waves, said feedback transducer being adapted to be positioned in said ear canal between said output transducer and said ear drum.

3. A noise suppressor according to claim 1 wherein said input transducer is adapted to be positioned in said ear canal adjacent said entrance and said output transducer is adapted to be positioned in said ear canal between said input transducer and said ear drum.

4. A noise suppressor according to claim 1 wherein said input transducer comprises:

a conductive layer defining a first capacitor electrode; and a diaphragm adjacent and spaced apart from said conductive layer, said diaphragm defining a second capacitor electrode such that said second capacitor electrode moves relative to said first capacitor electrode in response to said sound pressure waves, thereby generating said electrical signal.

5. A noise suppressor according to claim 1 wherein said output transducer comprises:

a conductive layer defining a first electrode; and a diaphragm adjacent and spaced apart from said conductive layer, said diaphragm defining a second electrode such that said second electrode moves relative to said first electrode in response to an output electrical signal applied therebetween, thereby producing said inverse noise pressure waves.

6. A noise suppressor according to claim 1 wherein said input transducer comprises an array of microelectromechanical input transducers.

7. A noise suppressor according to claim 1 wherein said output transducer comprises an array of microelectromechanical output transducers.

8. A noise suppressor according to claim 1 further comprising a processor for processing said electrical signal to generate an inverse noise signal which is applied to said output transducer.

9. A noise suppressor according to claim 8 wherein said processor comprises;

a filter for selectively passing a noise portion of said electrical signal, said noise signal being representative of said undesirable noise portion of said sound pressure waves; and an invertor for inverting said noise signal to generate said inverse noise signal.

10. A noise suppressor according to claim 9 wherein said filter blocks a ring-around portion of said electrical signal corresponding to said inverse noise pressure waves.

11. A noise suppressor according to claim 8 wherein said input transducer, said output transducer, and said processor are each provided on a common substrate.

12. A noise suppressor according to claim 1 wherein said inverse noise pressure waves are approximately equal in amplitude and 180° out of phase with respect to said undesired noise portion of said sound pressure waves.

13. A method of selectively reducing an undesired noise portion of sound pressure waves in an ear canal having an entrance and an ear drum, said method comprising the steps of:

providing a clear passage for said sound pressure waves from outside said ear canal to said ear drum;

generating an electrical signal in response to said sound pressure waves in said ear canal adjacent said entrance; and generating inverse noise pressure waves initiated from inside of said ear canal between said entrance and said ear drum, said inverse noise pressure waves being approximately out of phase with respect to said undesired noise portion of said sound pressure waves, thereby reducing said undesired noise portion, while allowing said sound pressure waves to pass from outside said ear canal to said ear drum.

14. A method according to claim 13 further comprising the step of selectively passing a noise portion of said electrical signal, said noise portion being representative of said undesirable noise portion of said sound pressure waves.

15. A method according to claim 14 further comprising the step of inverting said noise signal to generate an inverse noise signal which is representative of said inverse noise pressure waves.

16. A method according to claim 13 further comprising the step of generating an error signal in response to a combination of said sound pressure waves and said inverse noise pressure waves in said ear canal.

17. A method according to claim 13 wherein said inverse noise pressure waves are approximately equal in amplitude and 180° out of phase with respect to said undesired noise portion of said sound pressure waves.

18. A microelectromechanical noise suppressor for use in an ear canal, said microelectromechanical noise suppressor comprising:

a substrate which fits in the ear canal;

at least one microelectromechanical input transducer on said substrate for generating an electrical signal in response to sound pressure waves entering the ear canal; and at least one microelectromechanical output transducer on said substrate for producing inverse noise pressure waves approximately out of phase with respect to an undesired noise portion of said sound pressure waves, thereby reducing said undesired noise portion.

19. A microelectromechanical noise suppressor according to claim 18 wherein said at least one microelectromechanical input transducer comprises an array of input transducers on said substrate.

20. A microelectromechanical noise suppressor according to claim 18 wherein said at least one microelectromechanical output transducer comprises an array of output transducers on said substrate.

21. A microelectromechanical noise suppressor according to claim 18 further comprising a processor for processing said electrical signal to generate an inverse noise signal which is applied to said microelectromechanical output transducer.

22. A microelectromechanical noise suppressor according to claim 21 wherein said processor comprises a filter and an invertor.

23. A microelectromechanical noise suppressor according to claim 22 wherein said filter selectively passes a noise portion of said electrical signal, said noise portion being representative of said undesirable noise portion of said sound pressure waves.

24. A microelectromechanical noise suppressor according to claim 22 wherein said filter blocks a ring-around portion of said electrical signal corresponding to said inverse noise pressure waves.

25. A microelectromechanical noise suppressor according to claim 22 wherein said processor is on said substrate.

26. A microelectromechanical noise suppressor according to claim 18 wherein said inverse noise pressure waves are approximately equal in amplitude and 180° out of phase with respect to said undesired noise portion of said sound pressure waves.

27. A microelectromechanical noise suppressor for use in an ear canal, said noise suppressor comprising:

a substrate which fits in said ear canal;

at least one microelectromechanical input transducer on said substrate for generating an electrical signal in response to sound pressure waves;

at least one microelectromechanical output transducer on said substrate for producing inverse noise pressure waves approximately out of phase with respect to an undesired noise portion of said sound pressure waves, thereby reducing said undesired noise portion; and an acoustically unobstructing housing which supports said substrate, including said at least one microelectromechanical input transducer and said at least one microelectromechanical output transducer, in an ear canal having an entrance and an ear drum, wherein said acoustically unobstructing housing defines a clear passage for said sound pressure waves from said entrance of said ear canal to said ear drum.

28. A microelectromechanical noise suppressor according to claim 27 wherein said at least one microelectromechanical input transducer is adapted to be positioned in said ear canal adjacent said entrance and said at least one microelectromechanical output transducer is adapted to be positioned in said ear canal between said input transducer and said ear drum.

29. A microelectromechanical noise suppressor according to claim 28 further comprising a feedback transducer on said substrate adapted to be positioned in said ear canal between said output transducer and said ear drum.

30. A microelectromechanical noise suppressor comprising:

a substrate;

at least one microelectromechanical input transducer on said substrate for generating an electrical signal in response to sound pressure waves; and at least one microelectromechanical output transducer on said substrate for producing inverse noise pressure waves approximately out of phase with respect to an undesired noise portion of said sound pressure waves, thereby reducing said undesired noise portion;

wherein said microelectromechanical input transducer comprises:

a conductive layer on said substrate defining a first capacitor electrode; and a diaphragm adjacent and spaced apart from said conductive layer opposite said substrate, said diaphragm defining a second capacitor electrode such that said second capacitor electrode moves relative to said first capacitor electrode in response to said sound pressure waves, thereby generating said electrical signal.

31. A microelectromechanical noise suppressor comprising:

a substrate;

at least one microelectromechanical input transducer on said substrate for generating an electrical signal in response to sound pressure waves; and at least one microelectromechanical output transducer on said substrate for producing inverse noise pressure waves approximately out of phase with respect to an undesired noise portion of said sound pressure waves, thereby reducing said undesired noise portion;

wherein said microelectromechanical output transducer comprises:

a conductive layer on said substrate defining a first electrode; and a diaphragm adjacent and spaced apart from said conductive layer opposite said substrate, said diaphragm defining a second electrode such that said second electrode moves relative to said first layer in response to an output electrical signal applied therebetween, thereby producing said inverse noise pressure wave.

* * * * *